United States Patent [19]

Mikkelsen

[11] Plant 4,209

[45] Feb. 7, 1978

[54] KALANCHOE PLANT

[75] Inventor: James C. Mikkelsen, Ashtabula, Ohio

[73] Assignee: Mikkelsens, Inc., Ashtabula, Ohio

[21] Appl. No.: 766,737

[22] Filed: Feb. 8, 1977

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

A kalanchoe cultivar having a slow, compact growth habit, but being highly floriferous, bearing many small orange-red flowers on numerous shoots.

1 Drawing Figure

The present invention relates to a new and distinctive cultivar of kalanchoe plant, botanically known as kalanchoe and known by the cultivar name Pixie. The new cultivar was developed by me through controlled breeding by crossing the unpatented cultivar Red Empress (seed parent) with the cultivar Granat (pollen parent). Granat is disclosed in U.S. Plant Pat. No. 3,873, granted Apr. 27, 1976 to Norbert Bull. Asexual reproduction of the new cultivar by stem cuttings has shown that the unique features of this new kalanchoe are stabilized and are reproduced true to type in successive propagations.

The following characteristics distinguish the new kalanchoe from both its parent cultivars and other cultivated kalanchoes of this type known and used in the floriculture industry:

1. Better branching habits than for either parent, with the new cultivar thereby having greater potential for small plant production.

2. Slow compact growth resembles parent Red Empress. Cultivar was selected specifically for production in 7.5 cm. to 10 cm. pots. Plant vigor and keeping qualities are apparently derived from the pollen parent Granat.

3. Well clustered flowers, good placement, highly floriferous.

4. Small flowers are approximately the size of those of Red Empress, with an excellent proportion of flowers to the plant size. Granat has much larger flowers.

5. Flower color is darker orange red than Red Empress. The flowers of the pollen parent Granat are bright scarlet red.

6. Flowering time is 8–9 weeks after the start of flower initiation, with minimal difference between summer and winter flowering. This is similar to Red Empress but much faster than Granat.

7. The flower keeping quality is superior to that of either parent. In summer under high light and temperature conditions some fading may occur but without undue deterioration.

8. Stock plants may need applications of gibberellic acid to help elongate side shoots for maximum cutting production in periods of dark weather.

9. The foliage is superior in appearance and keeping qualities to that of Red Empress, and is similar except in size to Granat.

10. Flowers have slight tendency to close at night as does Red Empress and many other kalanchoe cultivars. Granat does not close at night.

The accompanying colored photograph illustrates the overall appearance of the new cultivar and shows the colors as true as it is reasonably possible to obtain in a color reproduction of this type.

The following is a detailed description of my new kalanchoe cultivar based on plants produced under commercial practices in the greenhouses of Mikkelsens Inc., Ashtabula, Ohio. The plant described and shown in the photograph was started with an unrooted cutting propagated directly in a 10 cm. plastic pot September 1st, placed into short day treatment September 30th without pinching, and flowering Dec. 12, 1976, and was grown on a capillary mat. Color references are made to the Royal Horticultural Society Colour Chart except where general terms of ordinary dictionary significance are used.

Parentage: A controlled pollination of Red Empress as the seed parent crossed with Granat as the pollen parent.

Propagation:

*Type cutting.*—Short tip cuttings up to 2 cm. long.

*Time to visible rooting.*—10 days at 21° C summer, 12–14 days at 21° C winter.

*Rooting habit.*—Quite rapid, profuse, dentritic.

Plant description:

*Form.*—Very short, compact, upright growth. The normal internodal spacing is only 5 or 6 mm. unless treated with gibberellic acid. The lower foliage near or at the soil line tends to deteriorate with such heavy growth.

*Habit of growth.*—Slow, upright, good branching.

*Foliage.*—Foliage is dense, dark green with tendency to crenate rather than entire as in Red Empress. Size: Mature foliage 7–8 cm. wide by 10 cm. long, petiole 15 mm. long. Shape: Generally elliptical to oblong. Texture: Glabrous, coriaceous. Margin: Crenate to slightly double crenate. Color: Mature foliage, top side yellow green 147A; underside yellow green 147B-C.

Flowering description:

*Flowering habit.*—Central or terminal flowers of small clusters in the cymes open in 8 weeks after start of flower initiation, other flowers open progressively with 1–2 weeks, with total flowering complete in approximately 12 weeks after short day treatment. Flowering will then be maintained for two or more additional months. Plant shown has eight internodal flowering shoots in addition to the terminal shoot, with 4–5 lateral flowering shoots being typical under the above described growing technique. Plant height is approximately 15 cm. high and 15 cm. in diameter.

*Natural flowering season.*—Late December. Flowering time under controlled daylength at 21° C in summer is 8–9 weeks; in winter is 9 weeks.

*Flower buds.*—Developing buds are elliptical up to 4 mm. long developing to tubular as flower petals mature, sheathed with four green sepals, corolla at maturity 10 mm. long.

*Flowers borne.*—Compound paniculate cymes on moderately strong peduncles 3–4 mm. in diameter and 10–12 cm. long; flower pedicels 1–1.5 mm. in diameter by 10 mm. long.

*Quantity of flowers.*—Highly floriferous, terminal cyme often has 100 or more flowers.

*Petals.*—Shape: Elliptical. Color: Top side, when opening brighter red than orange red 33A, fading to orange red 33B; under side orange red 33C-D. Number of petals: Form attached, 4 mm. in diameter; total flower diameter 10 mm.

*Reproductive organs.*—Stamens: Eight in number. Another shape: Flat elliptical disc, light brown in color. Filament color: Light green. Pollen color: Yellow. Pistils: Stigma shape: Flat crystalline, greenish while in color. Style color: Translucent green. Ovaries: Four in number, size 4 mm. long, light green in color.

Disease resistance: No diseases or adverse physiological problems observed to date, approximately 18 months after the initial discovery of the cultivar.

I claim:

1. A new and distinct cultivar of kalanchoe known by the cultivar name Pixie and particularly characterized as to uniqueness by the combined characteristics of slow, compact growth and excellent branching habits; highly floriferous, with well clustered, relatively small orange flowers; eight to nine week flowering time after flower initiation, and superior flower and foliage keeping qualities.

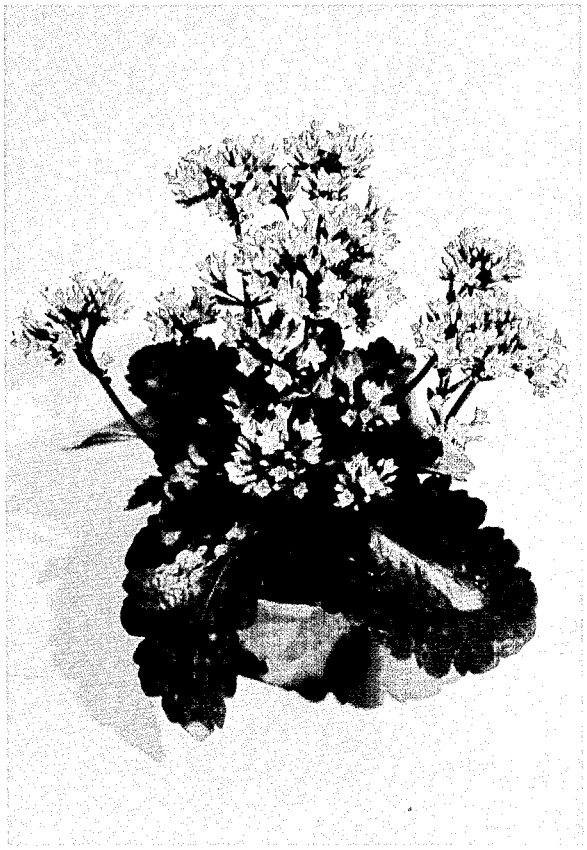

* * * * *